(12) United States Patent
Smith

(10) Patent No.: US 7,749,198 B2
(45) Date of Patent: Jul. 6, 2010

(54) SURGICAL PORTAL APPARATUS WITH VARIABLE ADJUSTMENT

(75) Inventor: Robert C. Smith, Middletown, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 44 days.

(21) Appl. No.: 12/124,688

(22) Filed: May 21, 2008

(65) Prior Publication Data

US 2008/0294114 A1    Nov. 27, 2008

Related U.S. Application Data

(60) Provisional application No. 60/931,244, filed on May 22, 2007.

(51) Int. Cl.
*A61M 5/178* (2006.01)

(52) U.S. Cl. .................................. 604/167.06

(58) Field of Classification Search ............ 604/167.06, 604/167.03, 246, 256, 167.01
See application file for complete search history.

(56) References Cited

U.S. PATENT DOCUMENTS

| | | | | |
|---|---|---|---|---|
| 5,209,737 A | * | 5/1993 | Ritchart et al. | ......... 604/167.03 |
| 5,300,035 A | | 4/1994 | Clement | |
| 5,354,280 A | | 10/1994 | Haber et al. | |
| 5,366,445 A | | 11/1994 | Haber et al. | |
| 5,385,552 A | | 1/1995 | Haber et al. | |
| 5,389,080 A | | 2/1995 | Yoon | |
| 5,391,153 A | | 2/1995 | Haber et al. | |
| 5,407,433 A | | 4/1995 | Loomas | |
| 5,411,515 A | | 5/1995 | Haber et al. | |
| 5,417,705 A | | 5/1995 | Haber et al. | |

(Continued)

FOREIGN PATENT DOCUMENTS

EP    0716862 A    6/1996

(Continued)

OTHER PUBLICATIONS

European Search Report for corresponding application EP 08251758—date of mailing is Sep. 18, 2008 (3 pages).

(Continued)

*Primary Examiner*—Nicholas D Lucchesi
*Assistant Examiner*—Brooke M Matney

(57) ABSTRACT

A surgical portal apparatus includes a portal member defining a longitudinal axis and having a longitudinal opening therethrough for receiving a surgical object, an adjustable seal disposed within the longitudinal opening and having inner seal portions adapted to permit passage of the surgical object in substantial sealed relation therewith and an adjustment member mounted within the portal member and operatively connected to the adjustable seal. The adjustment member is positioned to intersect the longitudinal passageway to engage the surgical object and move relative to the portal member to thereby cause corresponding relative displacement of the inner seal portions of the adjustable seal and facilitate passage of the surgical object through the adjustable seal. The inner seal portions of the adjustable seal are adapted for relative movement between a first generally approximated position and a second generally displaced position upon movement of the adjustment member. The inner seal portions of the adjustable seal may be dimensioned to substantially prevent passage of fluids when in the first generally approximated position. In one arrangement, the adjustable seal includes first and second seal elements which define the inner seal portions.

22 Claims, 6 Drawing Sheets

U.S. PATENT DOCUMENTS

| | | | |
|---|---|---|---|
| 5,429,609 A | 7/1995 | Yoon | |
| 5,441,486 A | 8/1995 | Yoon | |
| 5,484,418 A | 1/1996 | Quiachon et al. | |
| 5,492,304 A | 2/1996 | Smith et al. | |
| 5,496,280 A | 3/1996 | Vandenbroek et al. | |
| 5,545,142 A | 8/1996 | Stephens et al. | |
| 5,569,206 A | 10/1996 | Gorman, Jr. et al. | |
| 5,591,137 A | 1/1997 | Stevens | |
| 5,603,702 A | 2/1997 | Smith et al. | |
| 5,613,954 A | 3/1997 | Nelson et al. | |
| 5,628,732 A | 5/1997 | Antoon, Jr. et al. | |
| 5,634,908 A | 6/1997 | Loomas | |
| 5,657,963 A * | 8/1997 | Hinchliffe et al. | 251/149.1 |
| 5,693,025 A | 12/1997 | Stevens | |
| 5,697,913 A | 12/1997 | Sierocuk et al. | |
| 5,709,664 A | 1/1998 | Vandenbroek et al. | |
| 5,720,759 A | 2/1998 | Green et al. | |
| 5,752,938 A | 5/1998 | Flatland et al. | |
| 5,788,676 A | 8/1998 | Yoon | |
| 5,792,113 A | 8/1998 | Kramer et al. | |
| 5,814,026 A | 9/1998 | Yoon | |
| 5,820,600 A | 10/1998 | Carlson et al. | |
| 5,820,604 A | 10/1998 | Fox et al. | |
| 5,895,377 A | 4/1999 | Smith et al. | |
| 5,906,595 A | 5/1999 | Powell et al. | |
| 5,913,847 A | 6/1999 | Yoon | |
| 5,935,122 A | 8/1999 | Fourkas et al. | |
| 5,941,852 A | 8/1999 | Dunlap et al. | |
| 5,989,224 A | 11/1999 | Exline et al. | |
| 5,989,232 A | 11/1999 | Yoon | |
| 5,989,233 A | 11/1999 | Yoon | |
| RE36,702 E | 5/2000 | Green et al. | |
| 6,066,117 A | 5/2000 | Fox et al. | |
| 6,083,203 A | 7/2000 | Yoon | |
| 6,093,176 A | 7/2000 | Dennis | |
| 6,123,689 A | 9/2000 | To et al. | |
| 6,197,016 B1 | 3/2001 | Fourkas et al. | |
| 6,482,181 B1 | 11/2002 | Racenet et al. | |
| 6,514,260 B1 | 2/2003 | Zdeblick et al. | |
| 6,551,282 B1 | 4/2003 | Exline et al. | |
| 6,569,120 B1 | 5/2003 | Green et al. | |
| 6,595,946 B1 | 7/2003 | Pasqualucci | |
| 6,663,598 B1 | 12/2003 | Carrillo, Jr. et al. | |
| 6,702,787 B2 | 3/2004 | Racenet et al. | |
| 6,726,663 B1 | 4/2004 | Dennis | |
| 6,811,546 B1 | 11/2004 | Callas et al. | |
| 6,834,842 B2 | 12/2004 | Houde | |
| 6,863,661 B2 | 3/2005 | Carrillo, Jr. et al. | |
| 6,923,783 B2 | 8/2005 | Pasqualucci | |
| 6,942,671 B1 | 9/2005 | Smith | |
| 6,981,966 B2 | 1/2006 | Green et al. | |
| 7,011,314 B2 | 3/2006 | McFarlane | |
| 7,025,747 B2 | 4/2006 | Smith | |
| 7,083,626 B2 | 8/2006 | Hart et al. | |
| 7,101,353 B2 | 9/2006 | Lui et al. | |
| 7,112,185 B2 | 9/2006 | Hart et al. | |
| 7,153,319 B1 | 12/2006 | Haberland et al. | |
| 7,169,130 B2 | 1/2007 | Exline et al. | |
| 7,179,263 B2 | 2/2007 | Zdeblick et al. | |
| 7,235,062 B2 | 6/2007 | Brustad | |
| 7,244,244 B2 | 7/2007 | Racenet et al. | |
| 7,276,075 B1 | 10/2007 | Callas et al. | |
| 7,390,317 B2 | 6/2008 | Taylor et al. | |

FOREIGN PATENT DOCUMENTS

| | | |
|---|---|---|
| EP | 1671596 A | 6/2006 |
| GB | 2298906 A | 9/1996 |
| WO | WO93/01850 A | 2/1993 |
| WO | WO94/07552 A | 4/1994 |
| WO | WO01/89397 A | 11/2001 |

OTHER PUBLICATIONS

US 7,282,043, 10/2007, Racenet et al. (withdrawn)

* cited by examiner

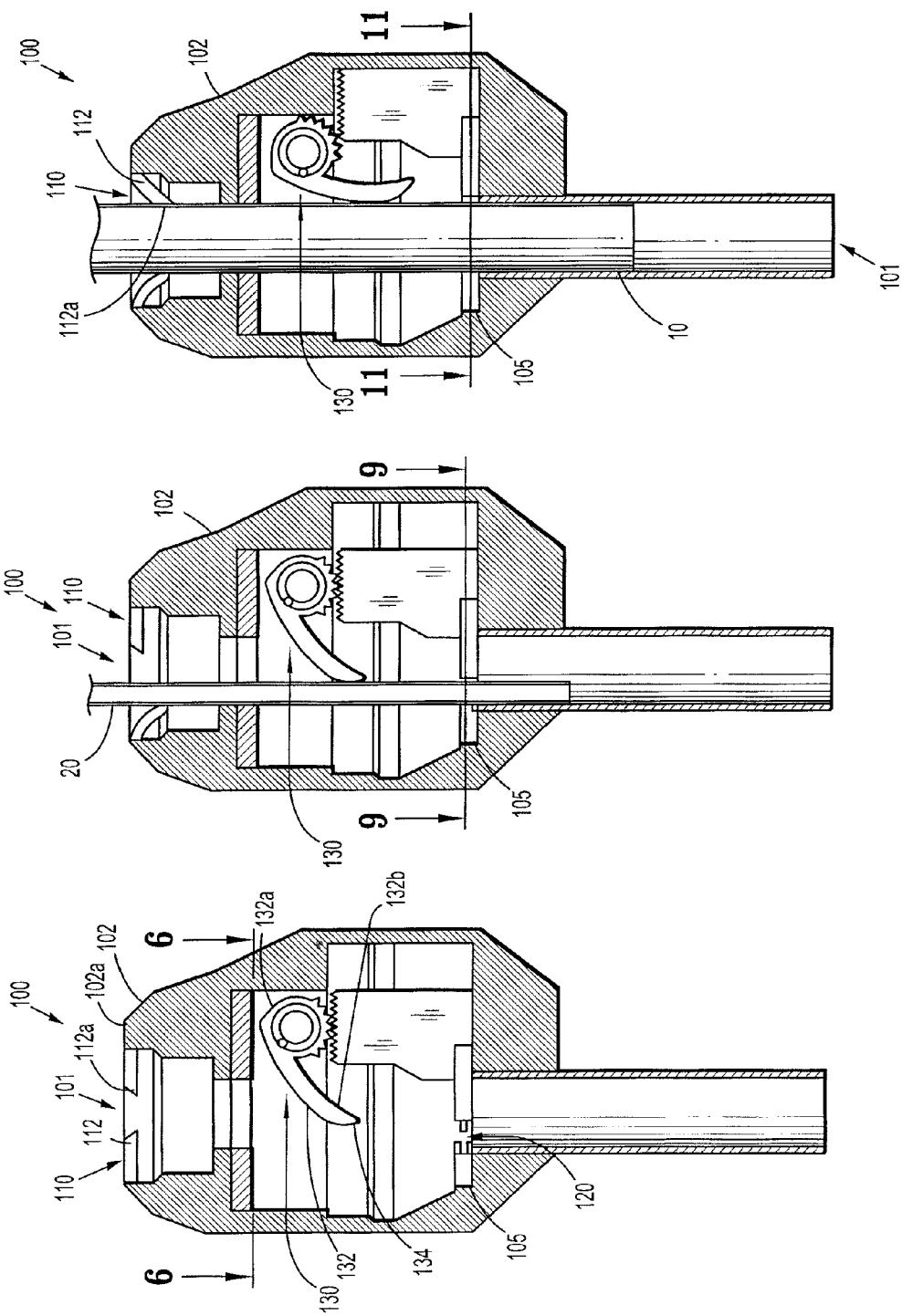

SURGICAL PORTAL APPARATUS WITH VARIABLE ADJUSTMENT

CROSS REFERENCE TO RELATED APPLICATION

The present application claims the benefit of and priority to U.S. Provisional Application Ser. No. 60/931,244 filed on May 22, 2007, the entire contents of which are incorporated herein by reference.

BACKGROUND

1. Technical Field

The present disclosure relates generally to a surgical portal apparatus for accessing the body, and more particularly, relates to a surgical portal apparatus having variable seal adjustment capabilities for receiving endoscopic instruments of various diameters.

2. Background of Related Art

Trocar assemblies and other surgical portal apparatuses are used by surgeons to operate on a patient without having to create large incisions that may become infected and may cause major scaring. Portal apparatuses are known in the art, as are the instruments inserted therethrough for operating within the body cavity. Typically a surgical portal apparatus comprises two major components, a trocar sleeve including a housing and a cannula, and an obturator.

Accessing the body cavity using a surgical portal apparatus is a multi-step process. An incision is initially made in the skin using a scalpel or other cutting instrument. Some trocar assemblies may include a cutting blade or sharpened distal end for performing this function. The obturator, having been inserted into the sleeve of the trocar cannula, is directed through the incision in the skin. The obturator is then used to penetrate the skin and access the body cavity. By applying pressure against the proximal end of the obturator, the sharpened point of the obturator is forced through the skin until it enters the body cavity. The cannula is inserted through the perforation made by the obturator and the obturator is withdrawn, leaving the cannula as an access way to the body cavity.

In order to provide a greater space in which a surgeon may operate and to increase visibility of the tissue being operated on, the body cavity is generally insufflated. To avoid gas leakage from within the cavity prior to or during insertion of an instrument through the cannula, and as instruments are being removed and replaced, various seal members have been developed. Conventional access systems generally include one or more seals configured for use with endoscopic instruments of the same or similar diameters. In this manner, the instruments inserted through the system must be of substantially similar diameter; otherwise a proper seal will not form between the instrument and the housing. An improper seal may result in leakage of insufflation gas.

However, not all endoscopic instruments have similar diameters. An instrument for performing a procedure may have a different diameter from a second instrument for performing the same procedure, just as instruments for performing various procedures may also have different diameters. Successful completion of a procedure may require the use of various instruments throughout the procedure. Thus, completing a procedure using multiple endoscopic instruments may require the use of multiple access systems, wherein system is configured for receiving an instrument of different diameter.

Therefore, it would be beneficial to have a surgical portal apparatus that is configured to sealingly receive endoscopic instruments of different diameters.

SUMMARY

Accordingly, a surgical portal apparatus includes a portal member defining a longitudinal axis and having a longitudinal opening therethrough for receiving a surgical object, an adjustable seal disposed within the longitudinal opening and having inner seal portions adapted to permit passage of the surgical object in substantial sealed relation therewith and an adjustment member mounted within the portal member and operatively connected to the adjustable seal. The adjustment member is positioned to intersect the longitudinal passageway to engage the surgical object and move relative to the portal member to thereby cause corresponding relative displacement of the inner seal portions of the adjustable seal and facilitate passage of the surgical object through the adjustable seal. The inner seal portions of the adjustable seal are adapted for relative movement between a first generally approximated position and a second generally displaced position upon movement of the adjustment member. The inner seal portions of the adjustable seal may be dimensioned to substantially prevent passage of fluids when in the first generally approximated position. In one arrangement, the adjustable seal includes first and second seal elements which define the inner seal portions.

The adjustment member may be operatively connected to the first seal element, whereby movement of the adjustment member upon engagement with the surgical object causes corresponding movement of the first seal element. The first seal element may be adapted for lateral movement relative to the longitudinal axis during movement between the first generally approximated position and the second generally displaced position. The adjustment member may be adapted for pivotal movement relative to the portal member. A gear member may be operatively connected to the adjustment member and to the first seal element. The gear member is adapted to translate movement of the adjustment member to corresponding movement of the first seal element.

The adjustment member may be adapted for movement between an initial position and an activated position. The initial position and the activated position correspond to the first generally approximated position and the second generally displaced position of the inner portions of the adjustable seal. The adjustment member includes a zero closure seal adapted to substantially close the longitudinal opening when in the first position of the adjustment member.

A secondary seal may be mounted to the portal member. The adjustable seal may be adapted to form a substantial seal about a surgical object having a first cross-sectional dimension and the secondary seal is adapted to form a substantial seal about a surgical object having a second cross-sectional dimension. The second cross-sectional dimension is greater than the first cross-sectional dimension. The adjustable seal may be adapted to form a seal about a surgical object having a diameter ranging from about 4 mm to about 6 mm, and wherein the secondary seal member is adapted to form a seal about a surgical object having a diameter ranging from about 9 mm to about 13 mm. The adjustable seal may be mounted distal to the secondary seal member.

The portal member may include a portal housing and a portal sleeve extending from the portal housing.

BRIEF DESCRIPTION OF THE DRAWINGS

The foregoing summary, as well as the following detailed description will be better understood when read in conjunction with the appended figures. For the purpose of illustrating the present disclosure, various embodiments are shown. It is understood, however, that the present disclosure is not limited to the precise arrangement and instrumentalities shown.

FIG. 3 is a side cross-sectional view of the surgical portal apparatus of FIGS. 1 and 2 illustrating the adjustment member, gear mechanism and the seal member with the adjustment member, in a first or initial condition;

FIG. 4 is a side cross-sectional view similar to the view of FIG. 3 illustrating an endoscopic instrument having a small diameter inserted therethrough;

FIG. 5 is a side cross-sectional view of the surgical portal apparatus illustrating the adjustment member in a second condition up insertion of an endoscopic device having a large diameter;

DESCRIPTION OF PREFERRED EMBODIMENTS

Figure 1:
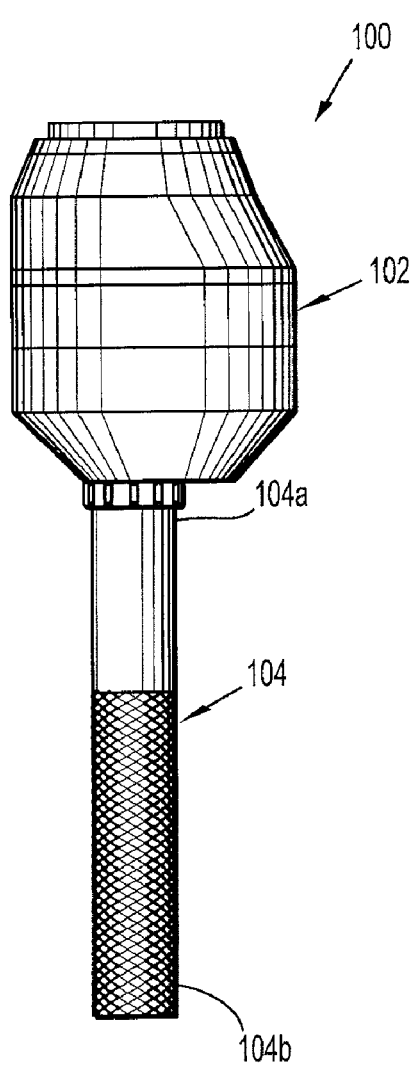
FIG. 1 is a side perspective view of a surgical portal apparatus according an embodiment of the present disclosure.

Referring now to the drawings wherein like reference numerals illustrate similar components throughout the several views, there is illustrated the surgical portal apparatus 100 in accordance with the principles of the present disclosure. As shown in the drawings and as described throughout the following description, as is traditional when referring to relative positioning on an object, the term "proximal" refers to the end of the apparatus which is closer to the user and the term "distal" refers to the end of the apparatus which is further from the user.

Figure 2:
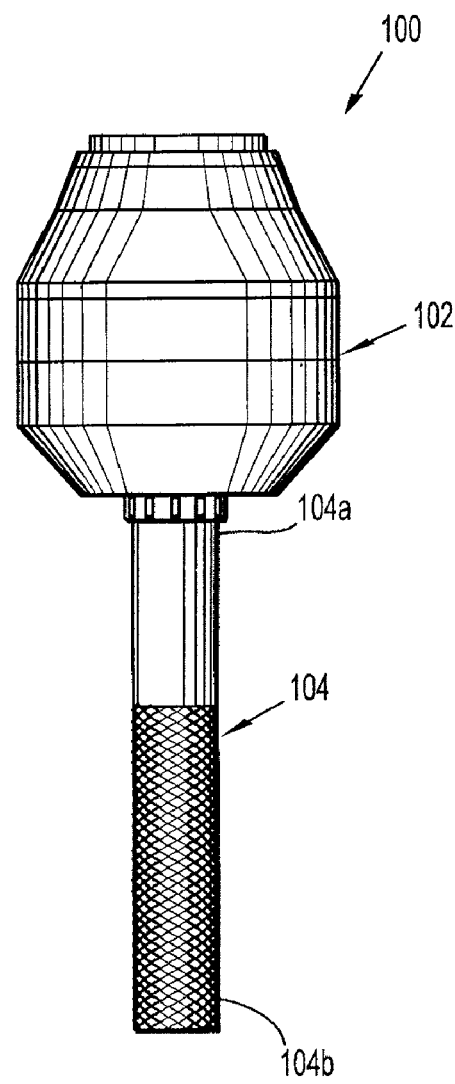
FIG. 2 is a front perspective view of the surgical portal apparatus of FIG. 1.

Referring initially to FIGS. 1 and 2, surgical portal apparatus 100 is shown in the form of a cannula assembly. Surgical portal apparatus 100 includes a housing or portal member 102 and a cannula sleeve 104 extending distally from housing 102. Surgical portal apparatus 100 may be configured for use with any known endoscopic or laparoscopic instrument. Cannula sleeve 104 is configured to be inserted through the skin into a body cavity with the aid of an obturator (not shown). Cannula sleeve 104 may instead include a blade or piercing tip for penetrating through the skin and into a body cavity. Cannula sleeve 104 may be integral formed with housing 102. Alternatively, cannula sleeve 104 may be configured for selectable engagement with housing 102.

Cannula sleeve 104 forms a substantially tubular member having proximal and distal ends 104a, 104b. Cannula sleeve 104 may be composed of plastic, metal, polymers or the like. Cannula 104 may be disposable, or in the alternative, reusable. Cannula sleeve 104 may be solid, or alternatively, cannula sleeve 104 may be flexible. Distal end 104b of cannula sleeve 104 may be open. Distal end 104b may instead be configured to include one or more seal members (not shown). Cannula sleeve 104 may be of any configuration and of any length or diameter. Thus, it is appreciated that the embodiments of the present disclosure are not limited by the configuration of cannula sleeve 104 and may be configured for use with any conceivable cannula assembly configuration.

Referring now to FIGS. 3-5, housing 102 of surgical portal apparatus 100 defines a passageway 101 therethrough configured for receiving endoscopic instruments of various diameters. Housing 102 includes a first seal member 110, a second seal member 120 and an adjustment member 130 therebetween. As will be described below, adjustment member 130 is operably connected to second seal member 120 such that movement of adjustment member 130 causes movement of second seal member 120.

First seal member 110 extends about an inner surface of housing 102, preferably about a proximal end 102a of housing 102. However, it is envisioned that first seal member 110 may be disposed anywhere along the length of passageway 101. First seal member 110 may comprise any known seal configurations. First seal member 110 may include one or more seal surfaces 112. First seal member 110 is configured for sealably receiving an endoscopic instrument 10 having a large diameter. Seal surface 112 may be formed of rubber, plastic, polymer or the like. An instrument contacting end 112a of seal surface 112 may be tapered to facilitated sealing about endoscopic instrument 10. Preferably, first seal member 110 is configured for sealably receiving an endoscopic instrument having the largest diameter capable of being inserted through passage 101.

Figure 6:
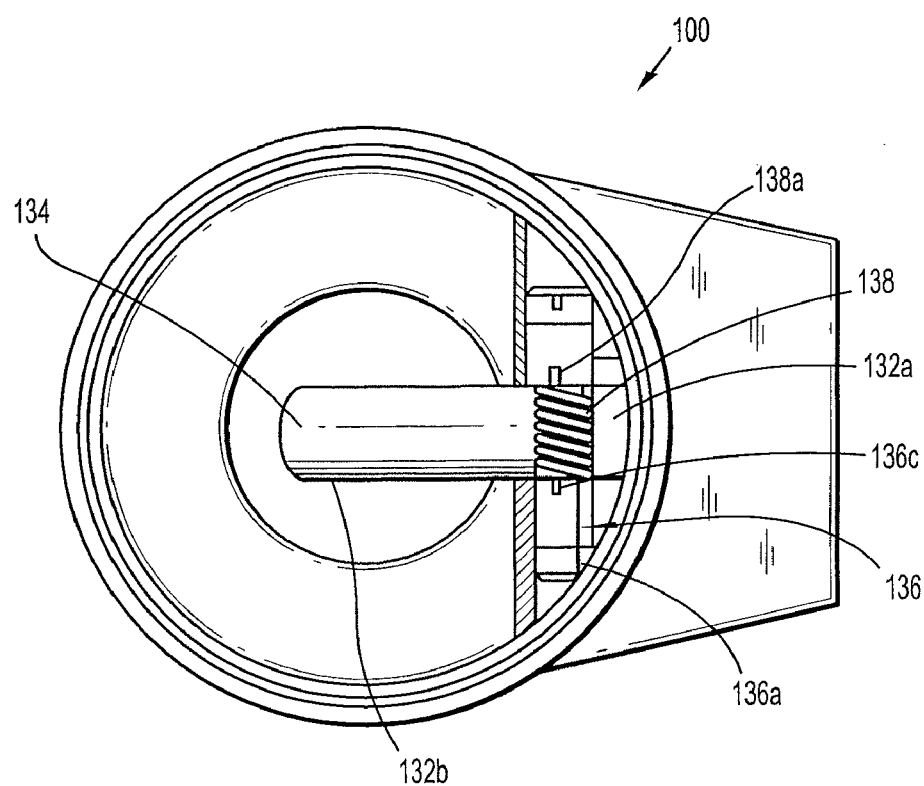
FIG. 6 is a view illustrating the adjustment member within the housing.

Still referring to FIGS. 3-5, adjustment member 130 defines a substantially planar base 132. Base 132 includes a first end 132a configured for pivotal engagement with housing 102 and a second end 132b configured to be pivotally biased within passageway 101. First end 132a of base 132 defines an opening 133 therethrough for pivotally receiving a bearing pin 136 (FIG. 6). Opening 133 includes first and second portions 133a, 133b. First portion 133a of opening 133 is configured to receive a first end 136a of bearing pin 136. Second portion 133b of opening 133 is larger than first portion 133a and is configured to receive a spring 138 about a second end 136b of bearing pin 136. A shoulder 137 (FIG. 7A) may be formed between first and second portions 133a, 133b of opening 133. Shoulder 137 defines an opening 137a therein for receiving a first end 138a of spring 138. Second end (not shown) of spring 138 is received within a slot 116c formed in second end 136b of bearing pin 136. Bearing pin 136, including spring 138 received about second end 116b, is inserted through opening 133 and is securely mounted to housing 102. The configuration of spring 138 within first end 132a of base 132 causes second end 132b thereof to be biasedly received within passageway 101 formed in housing 102.

Figure 7A:
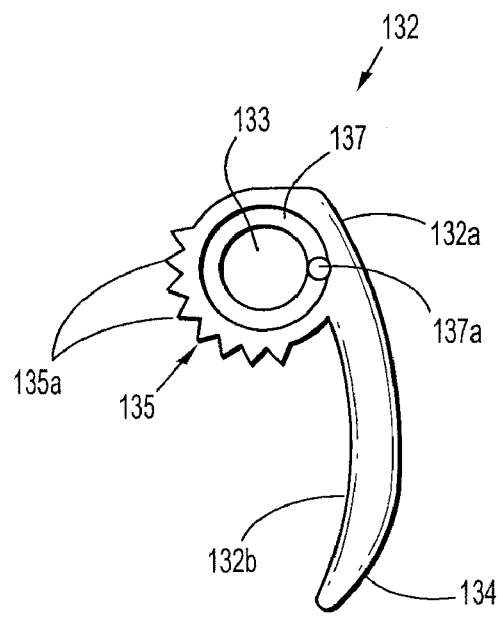
FIG. 7A is a side view of the adjustment member.
Figure 7B:
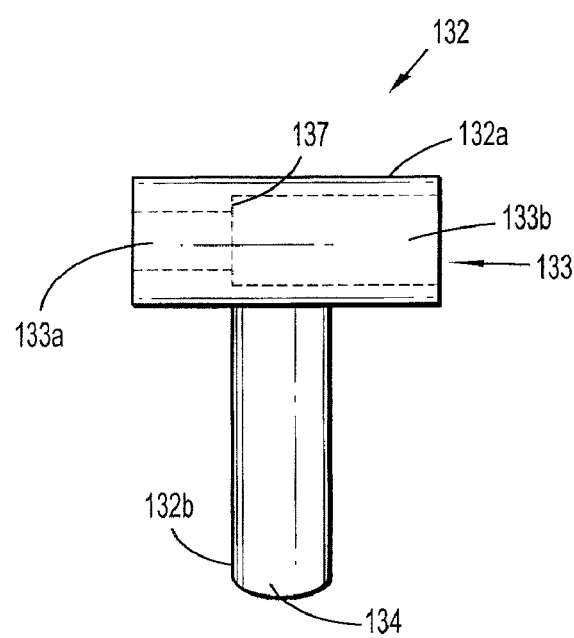
FIG. 7B is a top view of the adjustment member.
Figure 8A:
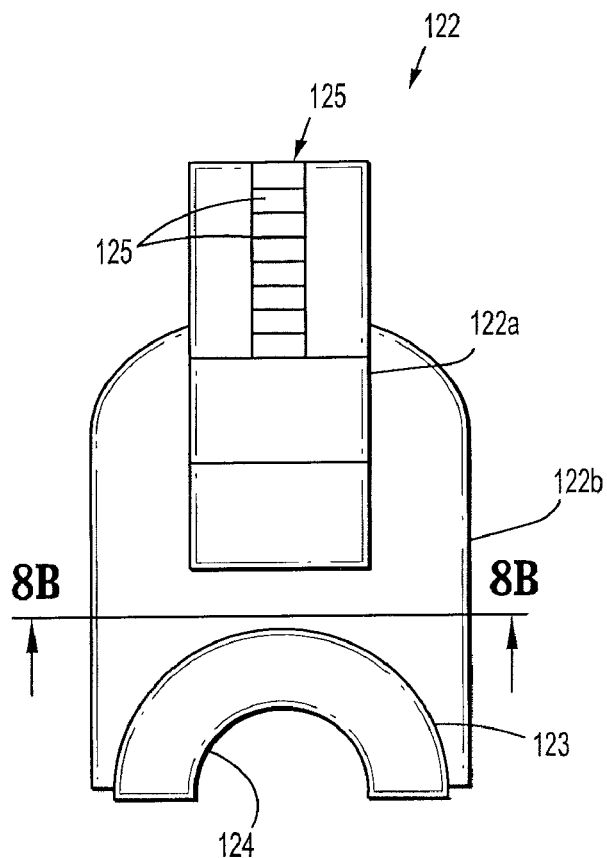
FIG. 8A is a top view of the second seal member.
Figure 8B:
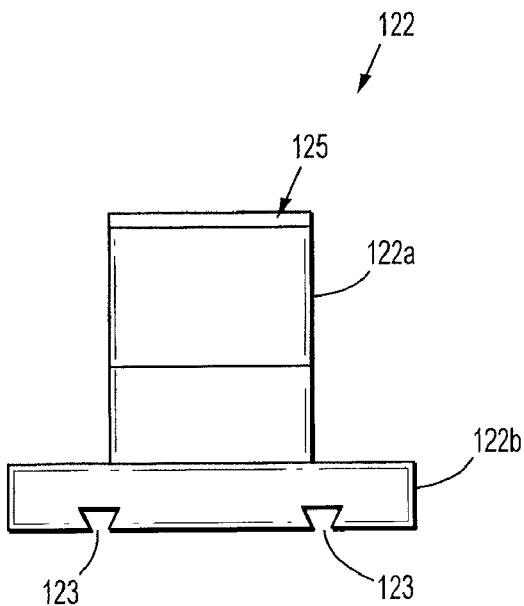
FIG. 8B is a side view of the second seal member.

Still referring to FIG. 7A, first end 132a of base 132 further includes a geared portion 135 radially extending at least partially about opening 133. Geared portion 135 includes gears 135a. Geared portion 135 is configured to engage a geared portion 125 formed in a base 122 of second seal member 120 (FIGS. 8A-8B). In this manner, geared portion 125 of second seal member 120 forms the rack to the pinion of geared portion 135 formed on adjustment member 130. As with all rack and pinion gears, rotational movement of the pinion gear causes lateral movement of the rack. Geared portion 135 may extend the width of first end 132*a* of base 132. Alternatively, geared portion 135 may comprise one or more rows of gears 135*a* for engaging one or more rows of gears 125*a* formed on first end 122*a* of base 122 (FIGS. 8A and 8B).

Base 132 of adjustment member 130 includes a second end 132*b* defining an instrument contacting surface 134. Second end 132*b* of base 132 is configured extend within passageway 101. As will be described below, second end 132*b* is configured to engage an endoscopic instrument 10, 20 as it is inserted through passageway 101 if the diameter of the instrument is larger then the opening formed in second seal member 120. As seen in FIGS. 4 and 5, contacting surface 134 of second end 132*b* may be rounded to prevent contact with endoscopic instrument 20 with the smaller diameter or facilitate engagement with endoscopic instrument 20 with the larger diameter.

Although as described, base 132 is biased received within passageway 101 by spring 138, it is envisioned that base 132 may be biased with any known means including, but not limited to, a hydraulic or pneumatic piston, flexible plate or the like.

Referring now to FIGS. 8A and 8B, second seal member 120 includes a base 122 having a first end 122*a* and a second end 122*b*. First end 122*a* of base 122 includes a substantially rectangular body including a geared portion 125. Geared portion 125 includes gears 125*a*. Gears 125*a* of geared portion 125 are configured to selectively engage gears 135*a* of geared portion 135 formed on first end 132*a* of base 132. As will be described below, geared portions 135, 125 are configured to such that second seal members 120 is opened as base 132 of adjustment member 130 is moved. Second end 122*b* of base 122 further defines one or more grooves 123 for slidably securing base 122 within housing 102. Housing 102 may define corresponding rails or tracks (not shown) configured to be received within grooves 123 formed in base 122.

Second end 122*b* of base 122 includes a substantially planar member defining a semi-circular opening 123. Second end 122*b* is configured to be received within a slot 105 formed in housing 102 (FIGS. 3-5). A seal surface 124 extends about opening 123. Seal surface 124 may comprise one or more layers. Seal surface 124 may be formed from rubber, plastic, polymer or the like. As will be described in detail below, second end 122*b* of base 122 is configured to operably engage slot 105 formed in housing 102 to form an adjustable opening 106*a* (FIG. 9A), 106*b* (FIG. 9B), 106*c* (FIG. 9*c*) for receiving endoscopic instruments of various diameters therethrough.

Figure 11:
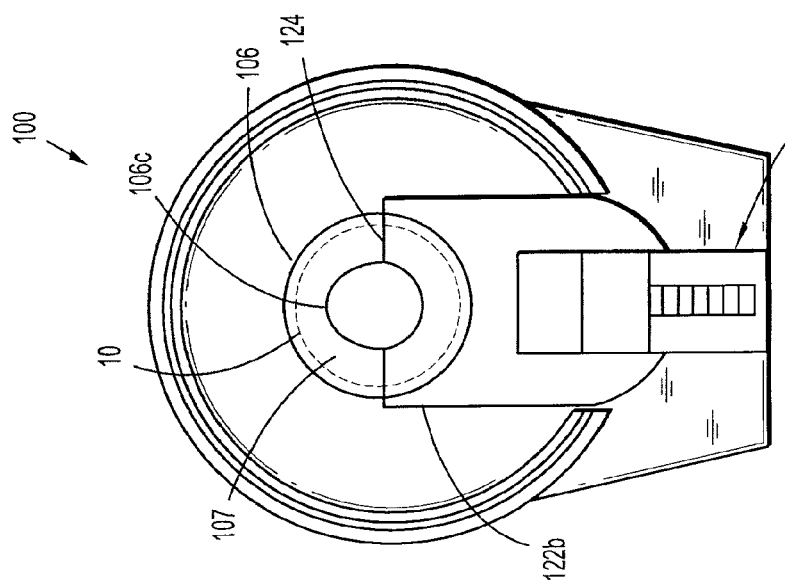
FIG. 11 is a view of the adjustment member in an activated position.
Figure 10:
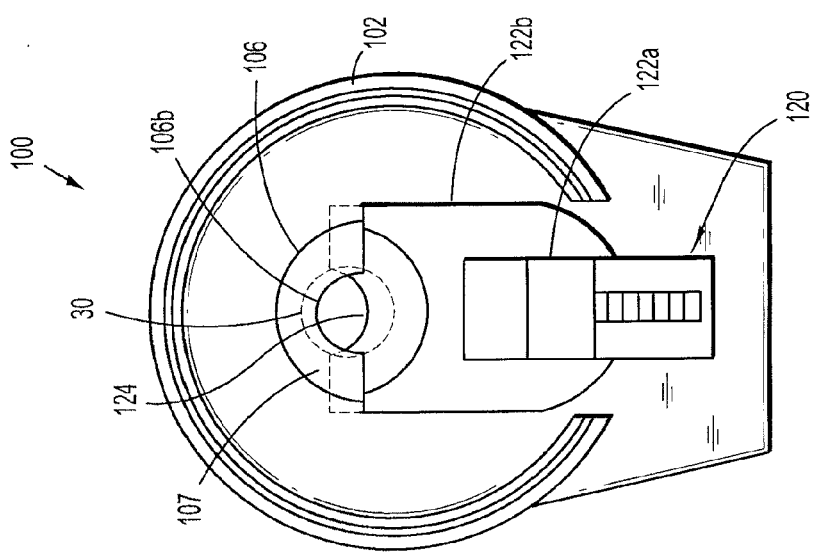
FIG. 10 is a view illustrating the adjustment member in an intermediate position.
Figure 9:
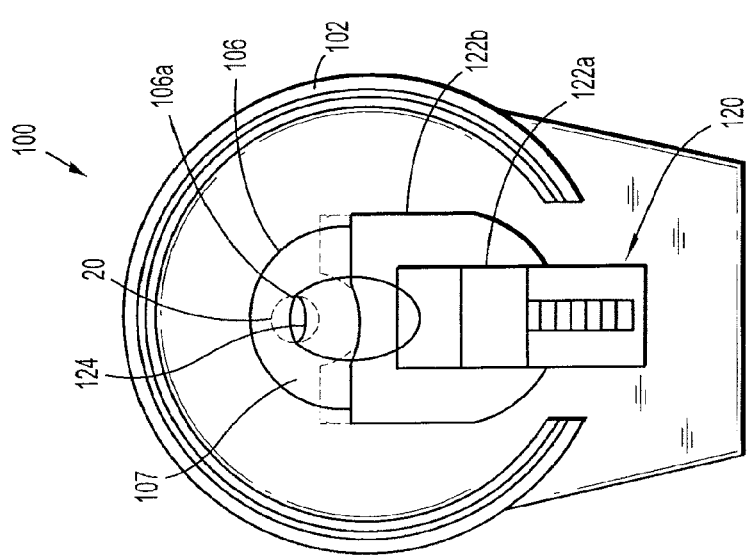
FIG. 9 is a view illustrating the adjustment member in the initial condition.

With reference to FIGS. 9-11, housing 102 defines a semi-circular opening 106 corresponding to opening 123 defined by base 122 of second seal member 120. Opening 106 includes a seal surface 107 extending thereabout for operable engagement with seal surface 124 of opening 123 to selectively form openings 106*a*-106*c* as adjustment member 130 is activated in the manner described below. Seal surfaces 124, 107 are configured to sealingly receive endoscopic instruments of increasing diameter as second seal member 120 is slidingly withdrawn from slot 105 formed in housing 102. Seal surfaces 124, 107 may alternatively include a flap or other means for sealing opening 106 with or without an endoscopic instrument 10, 20, 30 inserted therethrough.

With reference to FIGS. 3-5, surgical portal apparatus 100 will be described as relates to the operation of first and second seal members 110, 120 and adjustment member 130.

Referring initially to FIGS. 3 and 4, in a first or initial condition, base 132 of adjustment member 130 is pivotally biased within housing 102. Base 132 is configured and positioned such that endoscopic instrument 20 (FIG. 4) may pass through passageway 101 without engaging contacting surface 134 of second end 132*a*. In this manner, although geared portion 135 formed on base 132 engages geared portion 125 formed on base 122, base 122 remains slidingly received within slot 105 formed in housing 102 even as endoscopic instrument 20 is inserted past base 132. Endoscopic instrument 20 may incidentally contact seal surface 112 of first seal member 110, however, no sealing action is expected from this contact. In an alternate embodiment, seal surface 112 may be configured to sealingly receive endoscopic instrument 20.

With reference now to FIG. 9, in this first or initial condition, opening 106*a* is formed by semi-circular openings 106, 123 formed in housing 102 and base 122, respectively, and between seal surfaces 107, 124, respectively, for sealably receiving endoscopic instruments 10, 20, 30 therethrough. Alternatively, and as discussed above, in this first or initial condition, opening 106*a* may be sealed prior to insertion of instrument 20 therethrough.

Referring now to FIG. 5, in a second condition, base 132 of adjustment member 130 is completely pivoted from within passageway 101 by endoscopic instrument 10. Instrument 10 is initially inserted past first seal member 110 where it is sealingly engaged by seal surface 112. As instrument 10 engages contacting surface 134 formed on second end 132*b* of base 132, base 132 is pivoted from within passageway 101. The pivoting of base 132 causes geared portion 135 formed on first end 132*a* thereof to engage geared portion 125 formed on base 122 of second seal member 120. As base 132 of adjustment member 130 is pivoted geared portion 135 formed thereon engages geared portion 125 formed on base 122. The engagement of gears 125*a*, 135*a* caused by the pivoting of adjustment member 130 results in a corresponding lateral movement of second seal member 120. Downward pivoting of adjustment member 130 causes retraction or opening of second seal member 120, while upward pivoting of adjustment member 130 causes advancement or closing of second seal member 120.

With reference to FIG. 11, in the second condition, opening 106*c* formed by semi-circular openings 106, 123 and between seal surfaces 107, 124, respectively, for sealably receiving endoscopic instrument 10 therethrough. Opening 106 may be sized to receive an endoscopic instrument having a diameter of a size as small as endoscopic instrument 20 and as large as endoscopic instrument 10. Preferably, endoscopic instruments 10, 20, 30 measure 5 mm-12 mm in diameter, however, the aspects of the current disclosure may be modified to accommodate endoscopic instruments of larger and/or smaller diameter.

Figure 14:
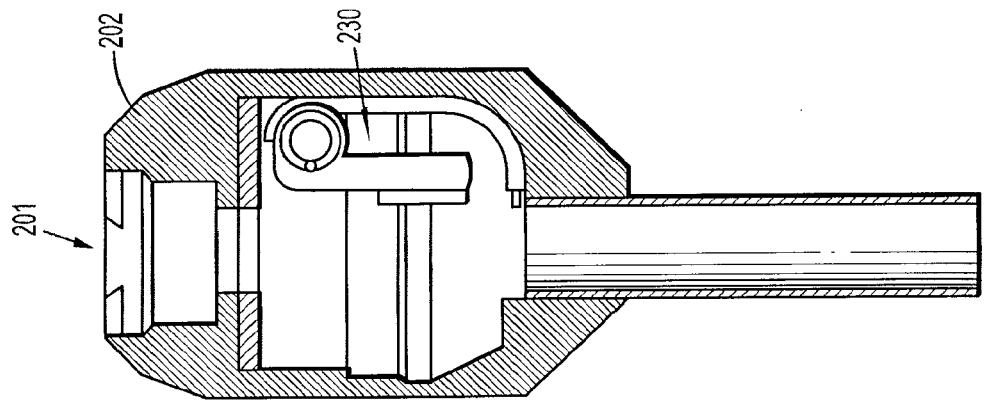
FIGS. 12-14 are cross-sectional views of a surgical portal apparatus according to another embodiment of the present disclosure, in a first or sealed condition (FIG. 12), in an intermediary condition (FIG. 13), and in an open condition (FIG. 14).
Figure 13:
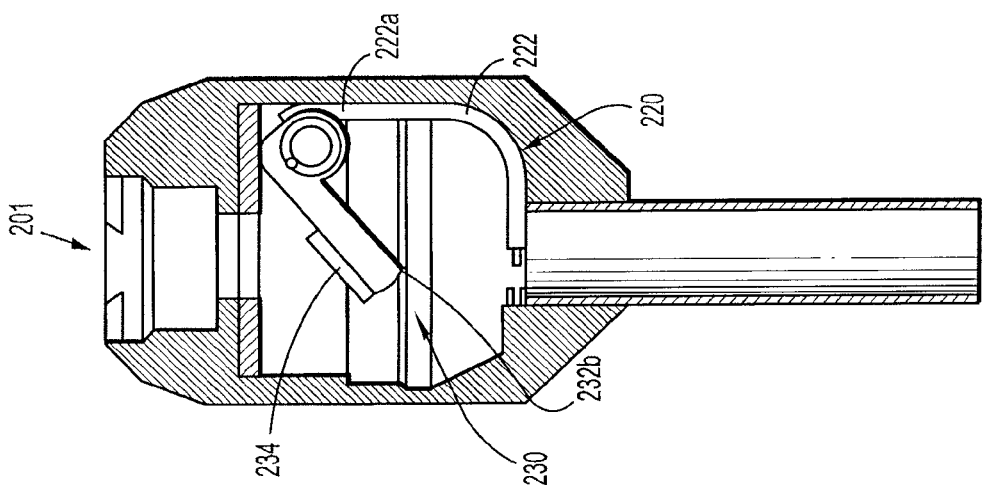
Figure 12:
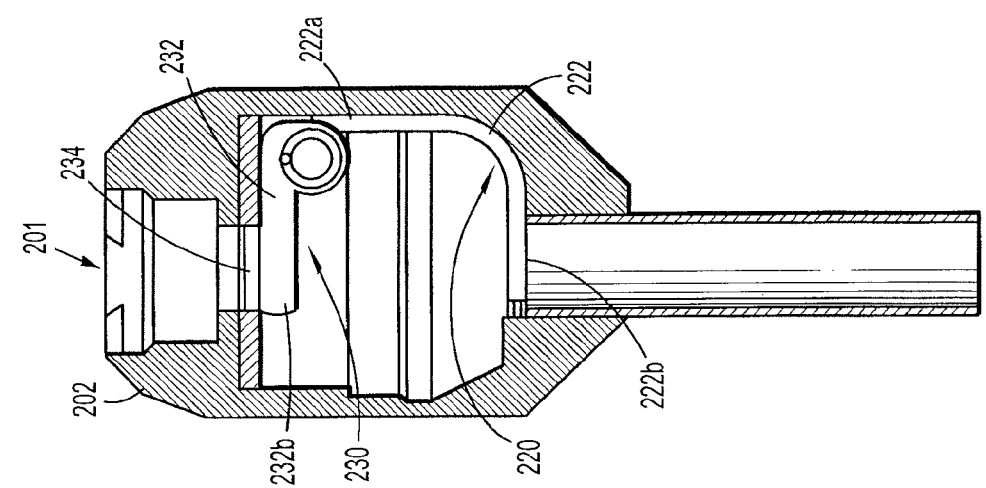

Referring now to FIGS. 12-14, an alternate embodiment of a surgical portal apparatus according to the present disclosure is shown generally as surgical portal apparatus 200. Surgical portal apparatus 200 is similar to surgical portal apparatus 100 and will only be described as relates to the differences therebetween. Surgical portal apparatus 200 includes a housing or portal member 202 and a cannula sleeve 204. Surgical portal apparatus 200 defines a passageway 201 therethrough for receiving endoscopic instruments of various diameters. A first seal member 210 is disposed about a proximal end of trocar housing 202, an adjustment mechanism 230 is pivotally mounted within housing 202, and a second seal member 220 is operably connected to adjustment mechanism 230.

Still referring to FIGS. 12-14, adjustment mechanism 230 is similar to adjustment member 130. Adjustment mechanism 230 differs from adjustment member 130 in the means by which adjustment mechanism 230 is operably connected to second seal member 220. Unlike the engagement of geared portions 125, 135, as described above, adjustment mechanism 230 is configured to lockingly receive an end of second seal member 220. In this manner, as adjustment mechanism 230 is pivotally opened as described above, second seal member 220 wraps about an end of adjustment mechanism 230, thereby retracting second seal member 220 from across passageway 201 formed in surgical portal apparatus 200.

Second seal member 220 includes a substantially planar base 222. Base 222 may comprise plastic, polymer, metal or the like. Base 222 includes first end 222a and a second end 222b. First end 222a is configured to be lockingly received by adjustment mechanism 230. Second end 222b is substantially similar in size and shape to second end 122b of base 122 described above. As discussed above, second seal member 220 is operably engaged with adjustment mechanism 230 such that downward pivotal movement of adjustment mechanism 230 causes lateral movement of second seal member from across passageway 201.

Furthermore, unlike adjustment member 130, second end 232b of base 232 may be configured to provide another sealing member 230. Second end 232b of base 232 may include a seal surface 234. Unlike in the previous embodiment, base 232 is completely biased across passageway 201. In this manner, sealing surface 234 extends across and within passageway 201, thereby forming a zero closure seal and effectively sealing passageway 201. As an endoscopic instrument (not shown) is inserted through trocar housing 202, base 232 of sealing member 230 is pivoted in the manner discussed above, thereby retracting second seal member 220, and opening passageway 201 for insertion of an instrument therethrough. Withdrawal of the endoscopic instrument causes sealing member 230 to return to a biased position across passageway 201 and results in the advancement of second seal member 220.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims append hereto.

What is claimed is:

1. A surgical portal apparatus, which comprises:
   a portal member defining a longitudinal axis and having a longitudinal passageway therethrough for receiving a surgical object;
   an adjustable seal disposed within the longitudinal passageway, the adjustable seal including first and second seal elements each having inner seal portions dimensioned and adapted to permit passage of the surgical object in substantial sealed relation therewith; and
   an adjustment member mounted within the portal member and positioned to intersect the longitudinal passageway to engage the surgical object and move relative to the portal member, the adjustment member being operatively connected to the second seal element such that, during movement of the adjustment member upon engagement with the surgical object, the second seal element moves relative to the first seal element and in a lateral direction second occurrance along an axis extending in orthogonal relation to the longitudinal axis to thereby cause corresponding relative displacement of the inner seal portions of the first and second seal elements and thereby facilitate passage of the surgical object through the adjustable seal.

2. The surgical portal apparatus according to claim 1 wherein the inner seal portions of the first and second seal elements of the adjustable seal are adapted for relative movement between a first generally approximated position and a second generally displaced position upon movement of the adjustment member and the second element.

3. The surgical portal apparatus according to claim 2 wherein the inner seal portions of the first and second seal elements of the adjustable seal are dimensioned to substantially prevent passage of fluids when in the first generally approximated position.

4. The surgical portal apparatus according to claim 2 wherein the portal member includes a portal housing and a portal sleeve extending from the portal housing.

5. The surgical portal apparatus according to claim 2 wherein the first seal element is secured to the portal member and the second seal element is independent of the first seal element, the second seal element adapted to translate within the longitudinal passageway of the portal member upon movement of the adjustment member.

6. The surgical portal apparatus according to claim 5 wherein the second seal element is adapted for lateral movement relative to the longitudinal axis during movement between the first generally approximated position and the second generally displaced position.

7. The surgical portal apparatus according to claim 5 wherein the adjustment member is adapted for pivotal movement relative to the portal member.

8. The surgical portal apparatus according to claim 5 including a gear member operatively connected to the adjustment member and to the second seal element, the gear member adapted to translate movement of the adjustment member to corresponding movement of the second seal element.

9. The surgical portal apparatus according to claim 5 wherein the adjustment member is adapted for movement between an initial position and an activated position, the initial position and the activated position corresponding to the first generally approximated position and the second generally displaced position of the inner portions of the adjustable seal.

10. The surgical portal apparatus according to claim 9 wherein the adjustment member includes a zero closure seal, the zero closure seal adapted to substantially close the longitudinal opening when in the first position of the adjustment member.

11. The surgical portal apparatus according to claim 9 wherein the adjustment member is normally biased toward the initial position thereof.

12. The surgical portal apparatus according to claim 5 including a secondary seal mounted to the portal member.

13. The surgical portal apparatus according to claim 12 wherein the adjustable seal is adapted to form a substantial seal about a surgical object having a first cross-sectional dimension and the secondary seal is adapted to form a substantial seal about a surgical object having a second cross-sectional dimension, the second cross-sectional dimension being greater than the first cross-sectional dimension.

14. The surgical portal apparatus according to claim 13 wherein the adjustable seal is adapted to form a seal about a surgical object having a diameter ranging from about 4 mm to about 6 mm, and wherein the secondary seal is adapted to form a seal about a surgical object having a diameter ranging from about 9 mm to about 13 mm.

15. The surgical portal apparatus according to claim 12 wherein the adjustable seal is mounted distal to the secondary seal.

16. A surgical portal apparatus, which comprises:
- a portal member defining a longitudinal axis and having a longitudinal passageway therethrough for receiving a surgical object;
- an adjustable seal disposed within the longitudinal passageway, the adjustable seal including:
  - a first seal element secured to the portal member and having inner seal surfaces; and
  - a second seal element independent of the first seal element and adapted to translate within the longitudinal passageway of the portal member in a lateral direction along an axis extending in orthogonal relation to the longitudinal axis and relative to the first seal element between an approximated position and a displaced position, the second seal element having inner seal surfaces cooperating with the inner seal surfaces of the first seal element to establish a general seal about the surgical object; and
- an adjustment member mounted for movement within the portal member and positioned to intersect the longitudinal passageway to engage the surgical object, the adjustment member operatively connected to the second seal element to cause movement of the second seal element from the approximated position to the displaced position during movement thereof within the portal member.

17. The surgical portal apparatus according to claim 16 including a rack and pinion associated with the second seal element and the adjustment member to cause movement of the second seal element between the approximated position and the displaced position.

18. The surgical portal apparatus according to claim 17 wherein the adjustment member is mounted for pivotal movement within the portal member.

19. The surgical portal apparatus according to claim 18 wherein the adjustment member is normally biased toward the initial position thereof.

20. The surgical portal apparatus according to claim 16 wherein the adjustment member is adapted for movement between an initial position and an activated position, the initial position and the activated position corresponding to the approximated position and the displaced position of the second seal element.

21. The surgical portal apparatus according to claim 20 wherein the adjustment member is dimensioned and configured to substantially close the longitudinal passageway of the portal member when in the initial position thereof.

22. The surgical portal apparatus according to claim 21 wherein the adjustment member is normally biased toward the initial position thereof.

* * * * *